(12) United States Patent
Cook et al.

(10) Patent No.: US 10,660,674 B2
(45) Date of Patent: May 26, 2020

(54) MAGNETICALLY LEVITATED SPINOUS PROCESS IMPLANTS AND METHODS THEREOF

(71) Applicant: Gomboc, LLC, Metairie, LA (US)

(72) Inventors: Stephen D. Cook, Metairie, LA (US); Samantha L. Salkeld, Metairie, LA (US)

(73) Assignee: Gomboc, LLC, Metairie, LA (US)

( * ) Notice: Subject to any disclaimer, the term of this patent is extended or adjusted under 35 U.S.C. 154(b) by 0 days.

(21) Appl. No.: 13/944,438

(22) Filed: Jul. 17, 2013

(65) Prior Publication Data
US 2014/0025122 A1   Jan. 23, 2014

Related U.S. Application Data

(60) Provisional application No. 61/672,384, filed on Jul. 17, 2012.

(51) Int. Cl.
*A61B 17/70* (2006.01)
*A61B 17/88* (2006.01)

(52) U.S. Cl.
CPC .......... *A61B 17/7062* (2013.01); *A61B 17/88* (2013.01)

(58) Field of Classification Search
CPC ...... A61F 2002/30079; A61F 2210/009; A61F 2/3836; A61B 17/7052; A61B 17/7062; A61B 17/7065; A61B 17/7014; A61B 2017/681; A61B 17/70; A61B 17/7071
USPC ........... 606/246, 279, 249; 623/17.11, 17.16
See application file for complete search history.

(56) References Cited

U.S. PATENT DOCUMENTS

| | | | | |
|---|---|---|---|---|
| 4,024,588 A | * | 5/1977 | Janssen | A61F 2/30 623/18.12 |
| 4,332,037 A | * | 6/1982 | Esformes | A61F 2/30 623/18.12 |
| 5,879,386 A | * | 3/1999 | Jore | A61F 2/38 623/16.11 |
| 6,387,096 B1 | * | 5/2002 | Hyde, Jr. | A61B 17/68 606/60 |
| 6,500,178 B2 | * | 12/2002 | Zucherman | A61B 17/7062 606/249 |
| 6,599,321 B2 | * | 7/2003 | Hyde, Jr. | A61N 2/06 623/18.12 |
| 6,695,619 B2 | * | 2/2004 | Brown-Wilkinson | G09B 23/34 434/274 |

(Continued)

FOREIGN PATENT DOCUMENTS

DE   28 21 678 A1   11/1979

OTHER PUBLICATIONS

Translation of DE 2821678 A1.*

(Continued)

*Primary Examiner* — Lynnsy M Summitt
(74) *Attorney, Agent, or Firm* — Haug Partners LLP

(57) ABSTRACT

A device for treatment of the spine comprising one or more vertebral attachments, in which the vertebral attachments contain one or more magnets that provide physiologic attractive or repulsive forces to affect the interaction between adjacent vertebrae. The vertebral attachments may also comprise one or more connecting components that affix the magnets to the vertebrae. In addition, there are methods for treatment of the spine comprising implantation of the device.

8 Claims, 16 Drawing Sheets

(56) References Cited

U.S. PATENT DOCUMENTS

| | | | | |
|---|---|---|---|---|
| 7,195,645 | B2* | 3/2007 | Disilvestro | A61B 5/076 600/587 |
| 7,637,927 | B2* | 12/2009 | Hyde, Jr. | A61B 17/70 606/279 |
| 7,717,959 | B2* | 5/2010 | William | A61F 2/4425 623/17.15 |
| 8,029,570 | B2* | 10/2011 | Barnes | A61B 17/58 623/18.12 |
| 8,114,158 | B2* | 2/2012 | Carl | A61F 2/4405 606/247 |
| 8,449,615 | B2* | 5/2013 | Fleischmann | A61F 2/38 623/17.16 |
| 8,801,796 | B2* | 8/2014 | Rogachefsky | A61F 2/4261 623/18.12 |
| 9,289,311 | B1* | 3/2016 | Whipple | A61F 2/4425 |
| 9,408,714 | B1* | 8/2016 | Whipple | A61F 2/4425 |
| 2003/0187510 | A1* | 10/2003 | Hyde | A61N 2/06 623/18.12 |
| 2003/0195633 | A1* | 10/2003 | Hyde, Jr. | A61B 17/68 623/18.12 |
| 2004/0068205 | A1* | 4/2004 | Zogbi et al. | 600/594 |
| 2004/0106995 | A1* | 6/2004 | Le Couedic | A61B 17/7062 623/17.11 |
| 2005/0251080 | A1* | 11/2005 | Hyde, Jr. | A61F 2/3836 602/26 |
| 2006/0036323 | A1* | 2/2006 | Carl | A61F 2/4405 623/17.11 |
| 2006/0079897 | A1* | 4/2006 | Harrison et al. | 606/61 |
| 2006/0247782 | A1 | 11/2006 | Molz, IV et al. | |
| 2007/0050030 | A1* | 3/2007 | Kim | A61B 17/7059 623/17.11 |
| 2007/0100457 | A1* | 5/2007 | Hyde, Jr. | A61B 17/88 623/18.12 |
| 2007/0162134 | A1* | 7/2007 | Marnay | A61F 2/4425 623/17.11 |
| 2007/0179493 | A1* | 8/2007 | Kim | A61B 17/7062 606/33 |
| 2007/0233251 | A1 | 10/2007 | Abdou | |
| 2008/0234733 | A1* | 9/2008 | Scrantz | A61B 17/7062 606/246 |
| 2008/0306324 | A1* | 12/2008 | Bonutti | A61N 2/02 600/12 |
| 2009/0024166 | A1* | 1/2009 | Carl | A61F 2/4405 606/247 |
| 2009/0076597 | A1* | 3/2009 | Dahlgren | A61B 17/7016 623/2.1 |
| 2009/0318976 | A1* | 12/2009 | Gabriel | A61B 17/68 606/283 |
| 2010/0036493 | A1* | 2/2010 | Simon | A61B 17/562 623/14.12 |
| 2010/0121381 | A1* | 5/2010 | Berta et al. | 606/246 |
| 2010/0280551 | A1* | 11/2010 | Pool et al. | 606/249 |
| 2011/0022091 | A1* | 1/2011 | Anderson et al. | 606/249 |
| 2011/0029020 | A1* | 2/2011 | Gordon et al. | 606/248 |
| 2011/0257749 | A1* | 10/2011 | Fleischmann | 623/17.16 |
| 2011/0257754 | A1* | 10/2011 | Fleischmann | A43B 1/0054 623/18.12 |
| 2012/0035661 | A1 | 2/2012 | Pool et al. | |
| 2013/0144340 | A1* | 6/2013 | Sheffer et al. | 606/249 |
| 2013/0165975 | A1* | 6/2013 | Tebbe et al. | 606/249 |
| 2013/0310937 | A1* | 11/2013 | Pimenta | A61F 2/4425 623/17.15 |
| 2014/0142700 | A1* | 5/2014 | Donner et al. | 623/17.11 |
| 2015/0005886 | A1* | 1/2015 | Pinneo | A61F 2/32 623/18.12 |

OTHER PUBLICATIONS

International Search Report and Written Opinion by the International Searching Authority, dated Oct. 31, 2013 in the PCT Application No. PCT/US2013/50929.

International Preliminary Report on Patentability, dated Jun. 2, 2015, in the PCT Application No. PCT/US2013/50929.

Extended European Search Report from the counterpart European Patent Application No. 13819480.8, dated Feb. 3, 2016.

\* cited by examiner

MAGNETICALLY LEVITATED SPINOUS PROCESS IMPLANTS AND METHODS THEREOF

CROSS REFERENCE TO RELATED APPLICATIONS

This application claims priority to U.S. provisional application Ser. No. 61/672,684 filed on Jul. 17, 2012, which is incorporated herein by reference.

FIELD OF THE INVENTION

The present invention relates to a device for treating the spine. The device may comprise one or more vertebral attachments, in which the vertebral attachments comprise one or more magnets that provide physiologic attractive or repulsive forces to affect the interaction between adjacent vertebrae. The vertebral attachments may also comprise one or more connecting components that affix the magnets to the vertebrae. The present invention additionally relates to methods of treating spinal stenosis and methods of controlling the interaction between adjacent vertebrae in the spine.

BACKGROUND OF THE INVENTION

Lumbar spinal stenosis is a narrowing of the spinal canal that occurs in the lower (lumbar) part of the spine. The narrowing of the spinal canal may reduce the space available for nerves to exit from the spinal canal due to compression of the spinal canal. When a nerve becomes pinched it can cause pain, tingling, weakness and numbness that may radiate from the lower back to the buttocks and legs.

Prior methods of treating spinal stenosis have included placing mechanical spacer(s) between two adjacent spinous processes. Without wishing to be bound by the theory, the spacer(s) provide relief by lifting and separating the two vertebrae off the pinched nerve by opening the spinal canal. However, current methods are not dynamic remedies that can adjust and adapt to the movement of the spine and the complex interaction that can occur between adjacent vertebrae.

SUMMARY OF THE INVENTION

The present invention relates to a device comprising one or more vertebral attachments. In some embodiments, the vertebral attachments comprise one or more magnets and one or more connecting components that can affix or attach the one or more magnets to vertebrae.

The one or more magnets may comprise magnetic material comprising rare earth metals and, in certain embodiments, a coating. The one or more connecting components may comprise extensions that are ring-shaped, oval-shaped, U-shaped, rod-shaped, etc., that can accommodate aspects of the vertebra, such as, for example, the spinous process. In combination with, or instead of, these extensions, the connecting components may also comprise one or more pins, screws, nails, or rods, or a combination thereof.

The present invention also relates to methods of treating spinal stenosis and/or methods of controlling or affecting the interaction between adjacent vertebrae in the spine in a patient. This interaction may involve separating, narrowing, or a combination thereof, the distance between adjacent vertebrae. These methods may comprise implanting the device of the invention, which may involve affixing or attaching the vertebral attachments to one or more adjacent vertebrae. In preferred embodiments, a single vertebral attachment is affixed to two or more vertebra. The magnets in vertebral attachments of adjacent vertebra may differ or have the same polarity, depending on the type of treatment for the patient. One or more magnets may be used on each vertebral attachment to provide a magnetic field to accommodate a desired dynamic interaction between adjacent vertebral attachments.

BRIEF DESCRIPTION OF THE FIGURES

For a more complete understanding of the invention, reference is made to the following description and accompanying drawings, as follows.

DETAILED DESCRIPTION OF THE INVENTION

Figure 1:
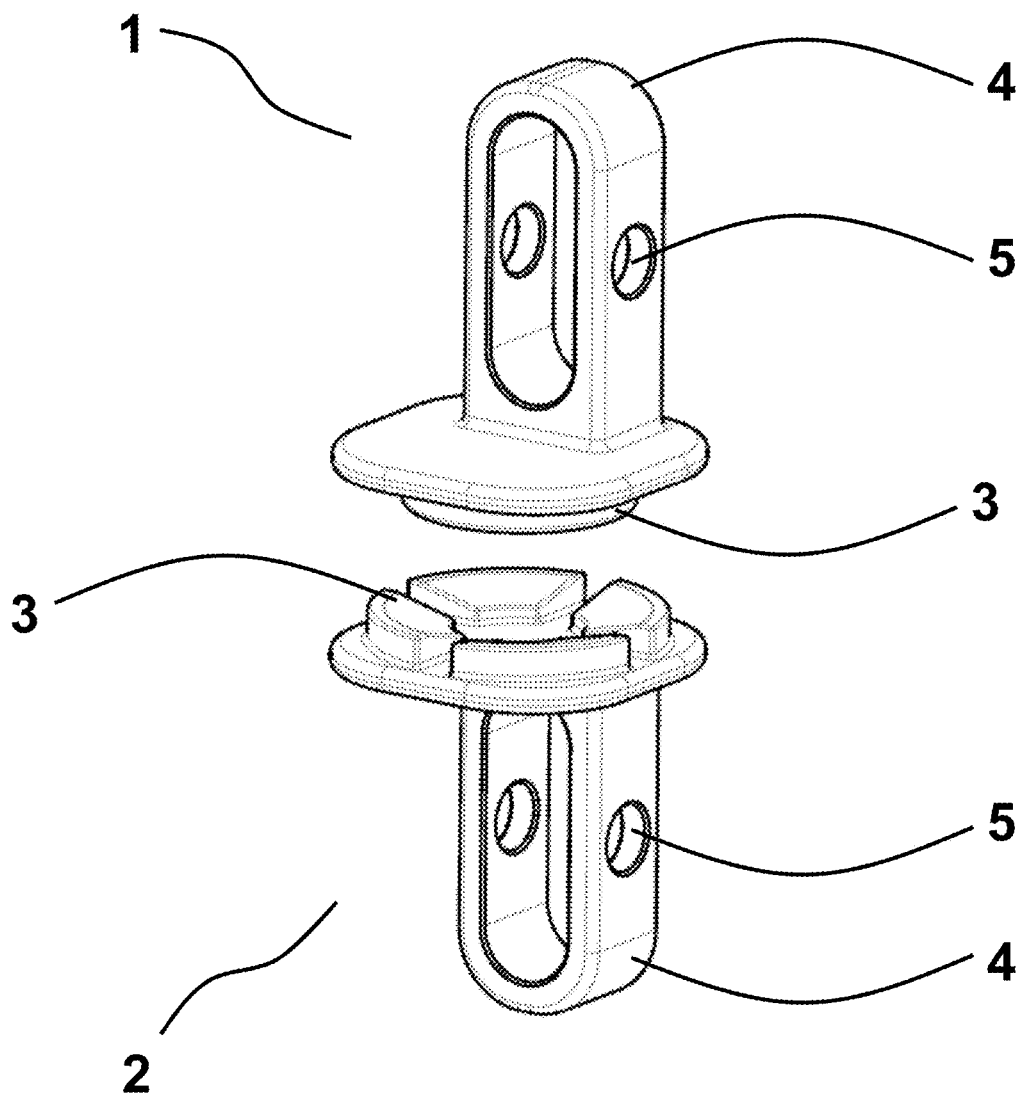
FIG. 1 is a device comprising vertebral attachments having a ring-shaped connecting component and an array of magnets according to embodiments of the invention.
Figure 2:
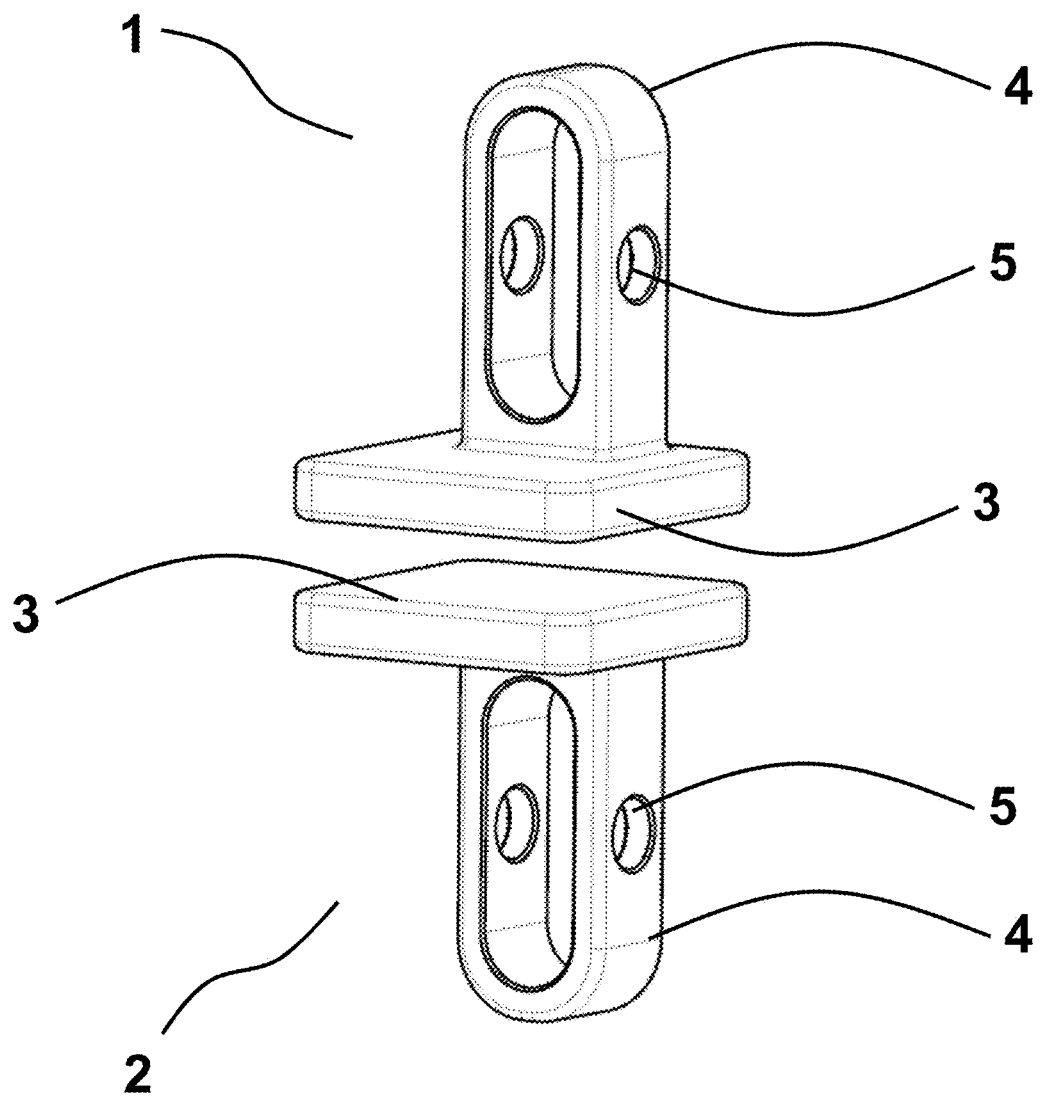
FIG. 2 is a device comprising vertebral attachments having a ring-shaped connecting component and a single magnet according to embodiments of the invention.

The present invention relates to an implant device for treatments involving the spine. For example, the device may be used to treat spinal stenosis, particularly lumbar spinal stenosis. The device may also generally be used to affect and/or control the interaction between adjacent vertebrae, such as the spacing between aspects of adjacent vertebrae. The device aims to provide constant relief on the nerve, possibly resulting in long term patient benefit.

The device of the invention utilizes magnets to provide the proper levitating (repulsive) force necessary to separate and maintain appropriate separation of the vertebral elements during physiologic loading, thereby reducing or eliminating the spinal stenosis. The levitating forces necessary may be as low as one half of a pound or as great as 25 pounds. The magnets and/or arrays of magnets also provide stability to the vertebral elements. This is accomplished by utilizing magnets and/or magnet arrays that generate magnetic fields that reduce or eliminate all out-of-plane forces which would tend to impart shear or rotational forces or undesirable forces to the vertebral elements. The magnets and/or array of magnets also generate magnetic fields that reduce or eliminate all out-of-plane forces which impart shear or rotation to the components (vertebral attachments) of the device. The magnets and/or array of magnets act to balance all in-plane and out-of-plane forces in order to provide the proper or desired axial levitating force.

The present invention further relates to methods of treating spinal stenosis and/or methods of controlling or affecting the interaction between adjacent vertebrae in the spine in a patient. The methods comprise implanting the device of the present invention.

Device for Treatment of the Spine

The device of the present invention may comprise two or more vertebral attachments, which may be separate components or a single assembled unit. The vertebral attachments can be affixed to different vertebrae, preferably adjacent to each other. In certain embodiments, a single vertebral attachment is affixed to a vertebra.

Each vertebral attachment may comprise a single or an array of magnets that impart the necessary physiologic attractive or repulsive forces desired from the device to affect the interaction between adjacent vertebrae, as well as provide position control and stability to the device. The magnets of the vertebral attachments may be of various shapes and cross-sections including, but not limited to, cylinders, squares, quadrilaterals, and or complete or partial rings.

The magnets may comprise any magnetic material. In some embodiments, the magnetic material may be formed of, may contain, or may be derived from rare earth metals, which may include, without limitation, scandium, yttrium, lanthanum, cerium, praseodymium, neodymium, promethium, samarium, samarium-cobalt, europium, gadolinium, terbium, dysprosium, holmium, erbium, thulium, ytterbium, lutetium, and combinations thereof. Such combinations may include, without limitation, neodymium-iron-boron (Nd—Fe—B), samarium-cobalt (Sm—Co), samarium iron nitride (Sm—Fe—N), cerium-cobalt permanent magnets (Ce $(CuCo)_5$). The magnetic material may also be formed of, may contain, or may be derived from other permanent magnets or magnetic materials including, without limitation, alnico alloys (Al—Ni—Co V), platinum-cobalt alloys (Pt—Co), iron-based alloys such as iron-cobalt (FeCo), iron-platinum (FePt), hard ferrites such as barium ferrite ($BaFe_{12}O_{19}$) or strontium ferrite ($SrFe_{12}O_{19}$), magnetic shape memory alloys such as (Ni—Mn—Ga), manganese-bismuth permanent magnets (MnBi), and cobalt-nickel-chromium alloys (Co—Ni—Cr).

In certain embodiments, the magnets of the vertebral attachments may comprise one or more coatings or surface treatments that may increase the biocompatibility of the magnets. Suitable coatings or surface treatments may be applied by various methods such as spraying, painting, and the like. The coatings or surface treatments may have a thicknesses generally ranging from about 100 nanometers to about 1 millimeter. Examples of such coatings and surface treatments may include, without limitation, nickel plating (nickel-copper-nickel), gold, titanium, titanium nitride, chromium nitride, palladium, stainless steel, polytetrafluoroethylene (often sold under the DuPont trademark Teflon™), and the like. The magnets may also be encased in a shell of any suitable biocompatible materials such as titanium and titanium alloys, cobalt chromium alloy, stainless steel, etc or biocompatible polymeric materials such as polyether ether ketone (PEEK), polyether ketone ketone (PEK) polymers, polyethylenes, etc. In various embodiments, any of the magnets disclosed herein may be a nickel-plated (Ni—Cu—Ni), gold-coated neodymium (NdFeB) N52-grade magnet.

In addition to the magnets, the vertebral attachment may also comprise one or more connecting components, which affix the one or more magnets of the vertebral attachment to the vertebra. These connecting components may be comprised of any suitable metallic biomaterial such as titanium, titanium alloy, cobalt chromium alloy, stainless steel, etc., or polymeric materials such as polyether ether ketone (PEEK), etc.

The connecting component may comprise extensions that are ring-shaped, oval-shaped, U-shaped, rod-shaped, etc. (i.e., in a shape that resembles a ring, an oval, a "U," a rod, etc.), which can accommodate aspects of the vertebra, such as, for example, the spinous process. The connecting component may also comprise one or more pins, screws, nails, rods, or other mechanical devices that can be used to affix or attach the extension to the vertebra. In some embodiments, the connecting component may be a combination of extensions as listed above with pins, screws, rods, keels, etc. In such embodiments, the extensions may comprise holes, slots, etc., which can accommodate the pins, screws, rods, keels, etc. In certain embodiments, the bone interfacing surfaces of the connecting components may have a porous metal coating, a plasma-sprayed coating, and/or hydroxyapatite coating, or a roughened surface to enhance fixation of the vertebral attachment to the spine.

The connecting component may be of a size and shape suitable for implantation and attachment to the vertebrae of the spine. Similarly, the vertebral attachment in general may be of a size and shape suitable for implantation and treatment of the spine.

Figure 3:
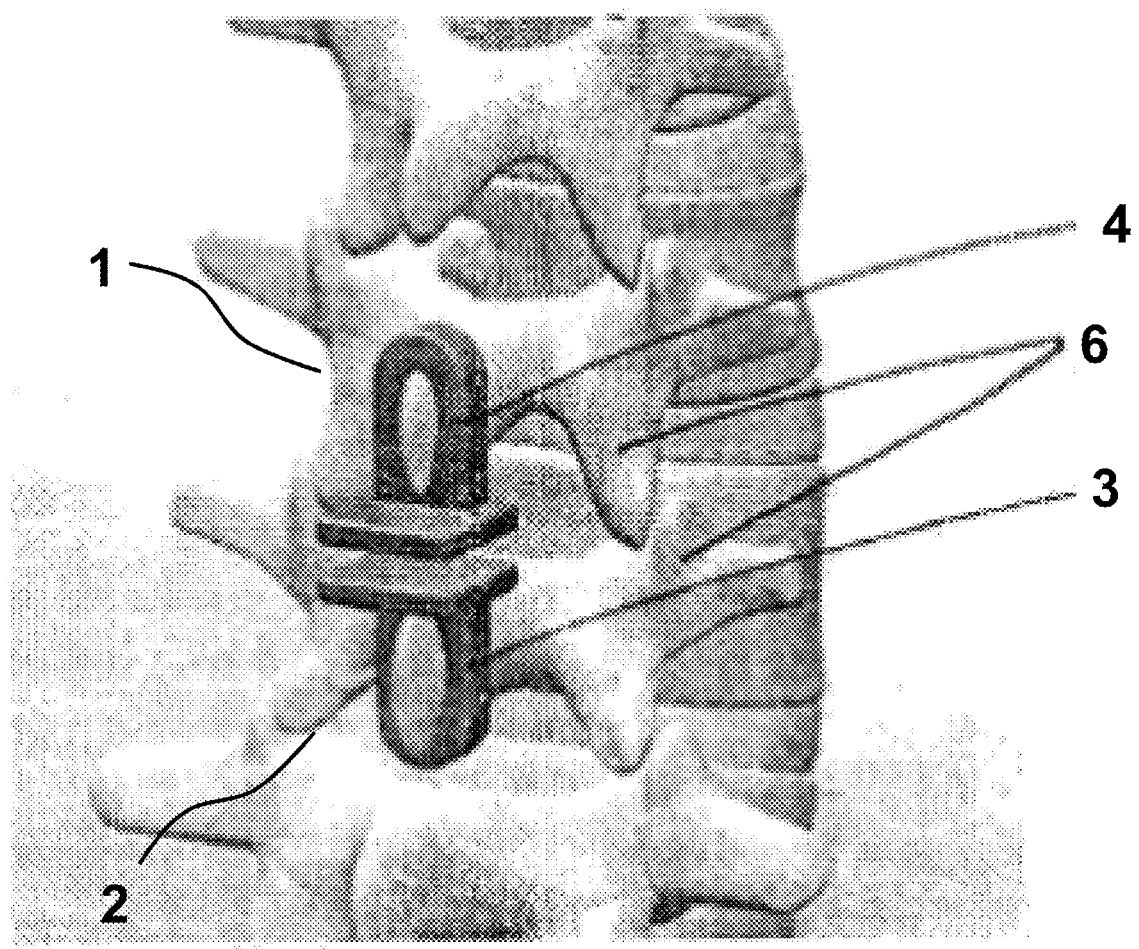
FIG. 3 is a posterior/side view of a device affixed to vertebrae, in which the device comprises vertebral attachments having a ring-shaped connecting component and a single magnet according to embodiments of the invention.
Figure 4:
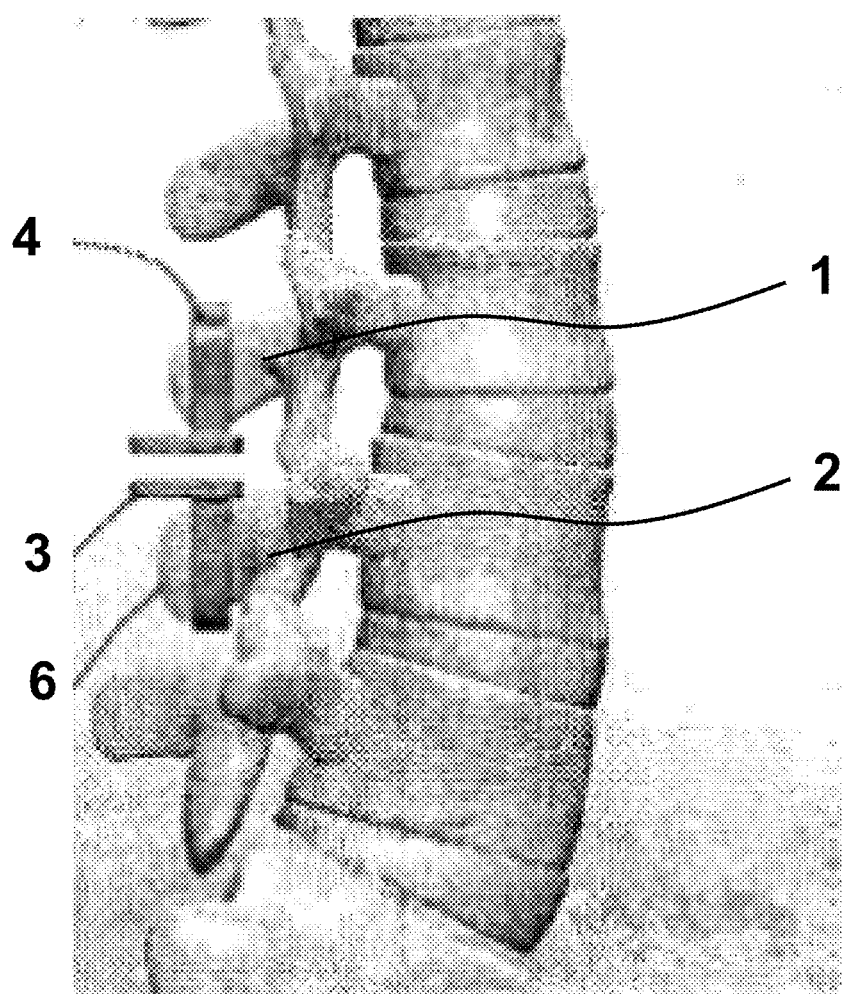
FIG. 4 is a side view of a device affixed to vertebrae, in which the device comprises vertebral attachments having a ring-shaped connecting component and a single magnet according to embodiments of the invention.
Figure 5:
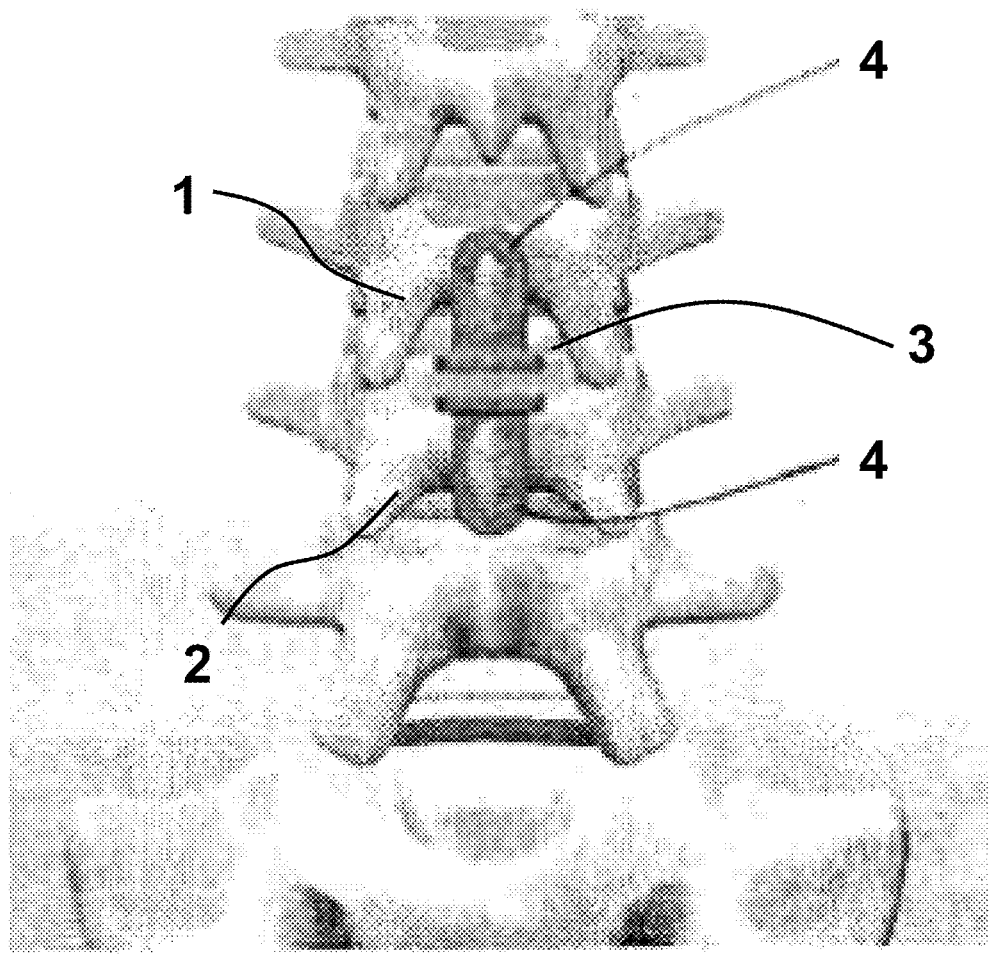
FIG. 5 is a posterior view of a device affixed to vertebrae, in which the device comprises vertebral attachments having a ring-shaped connecting component and a single magnet according to embodiments of the invention.

FIGS. 1-11 each show two vertebral attachments according to embodiments of the invention that are designed to be affixed to adjacent vertebrae. The first vertebral attachment 1 is to be affixed to the superior vertebra, while the second vertebral attachment 2 is to be affixed to the inferior vertebra. Each vertebral attachment comprises one or more magnets 3, and a connecting component 4. In FIGS. 1-5, the connecting components comprise ring-shaped extensions 4 and, in the embodiments illustrated here, comprise holes 5 that can accommodate a rod or the like to help affix the vertebral attachment to the vertebra. However, in FIG. 1 the vertebral attachments 1 and 2 comprise an array of magnets 3 in the shape of partial rings, while in FIGS. 2-4 the vertebral attachments 1 and 2 comprise a single magnet 3 in the shape of a quadrilateral. FIGS. 3-5 show the fixation of the vertebral attachments of FIG. 2 to the vertebrae 6.

Figure 6:
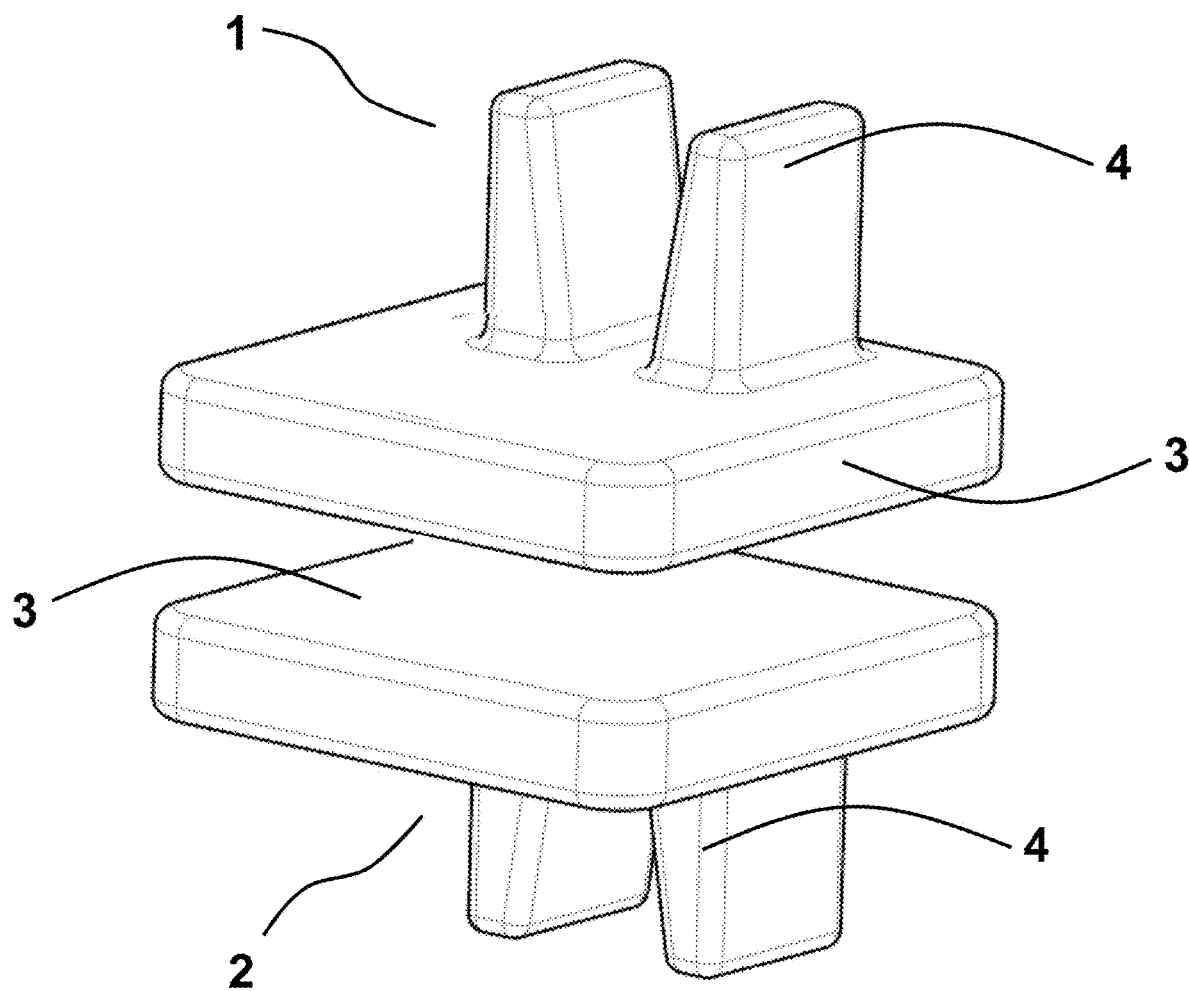
FIG. 6 is a device comprising vertebral attachments having a U-shaped connecting component and a single magnet according to embodiments of the invention.
Figure 7:
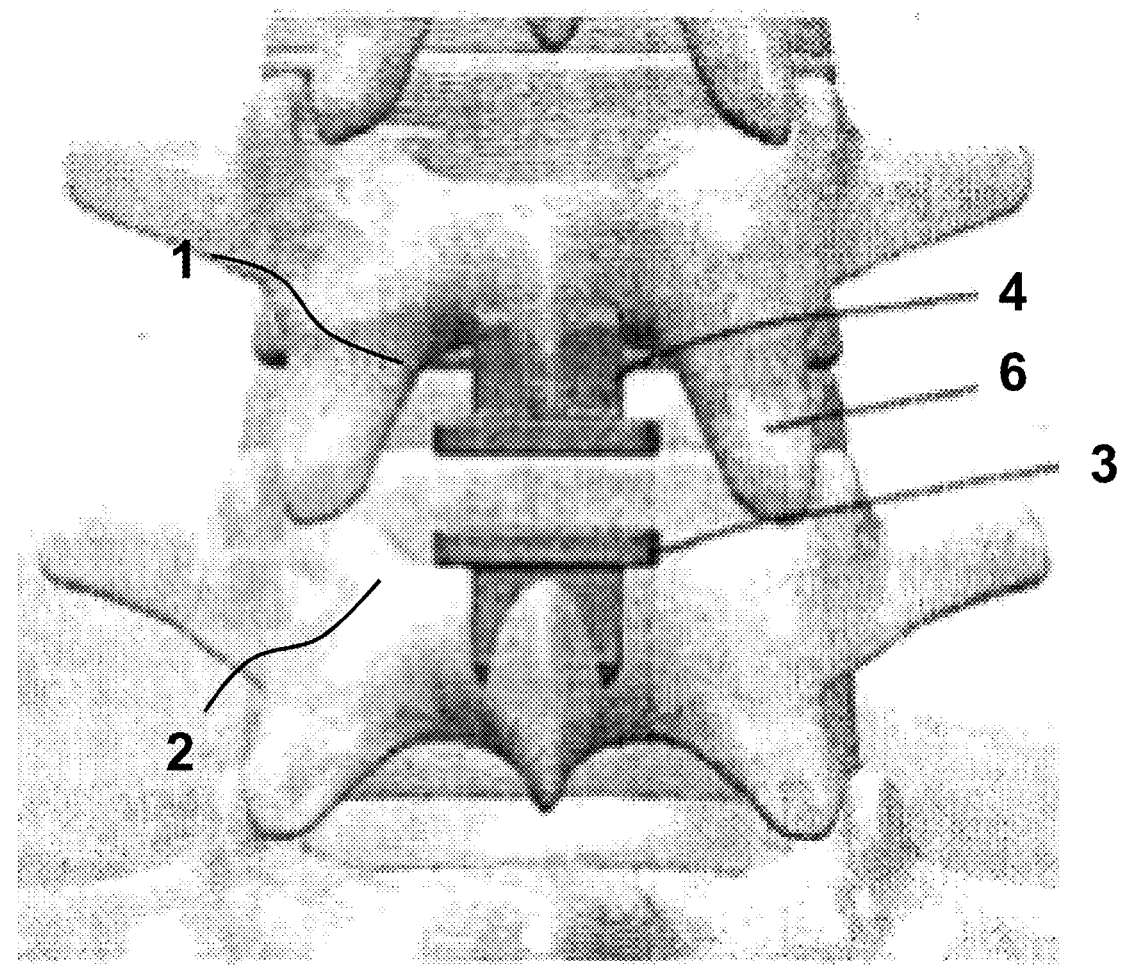
FIG. 7 is posterior view of a device affixed to vertebrae, in which the device comprises vertebral attachments having a U-shaped connecting component and a single magnet according to embodiments of the invention.
Figure 8:
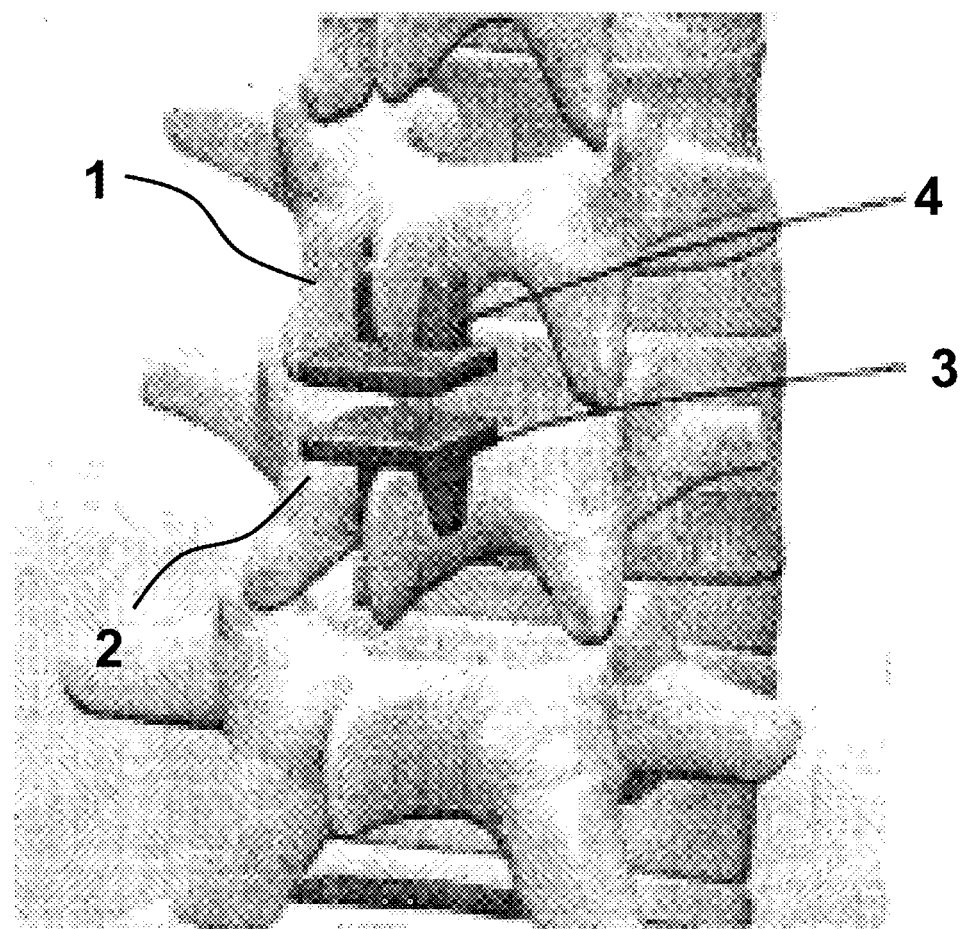
FIG. 8 is a posterior/side view of a device affixed to vertebrae, in which the device comprises vertebral attachments having a U-shaped connecting component and a single magnet according to embodiments of the invention.
Figure 9:
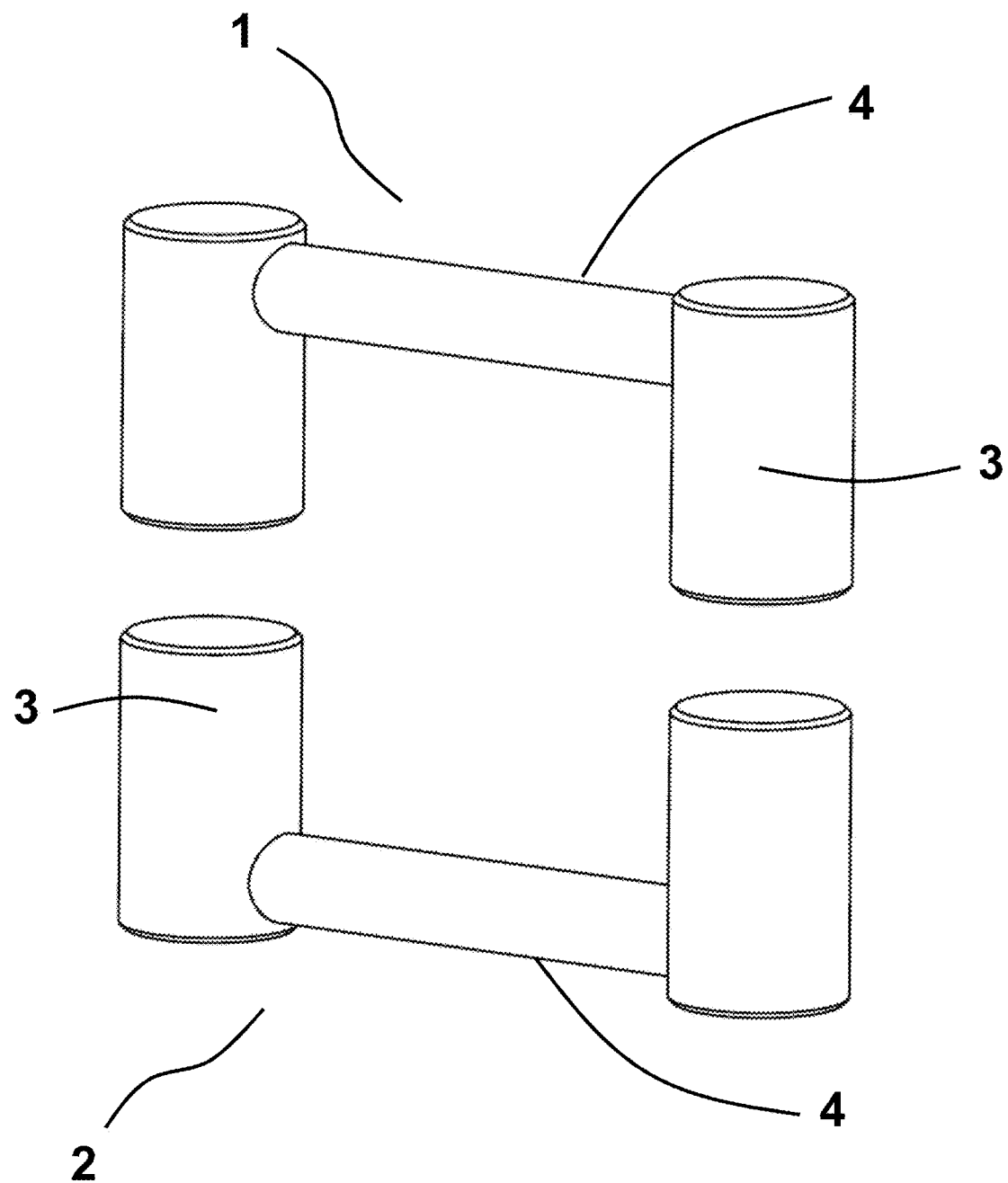
FIG. 9 is a device comprising vertebral attachments having a rod-shaped connecting component and pairs of magnets according to embodiments of the invention.
Figure 10:
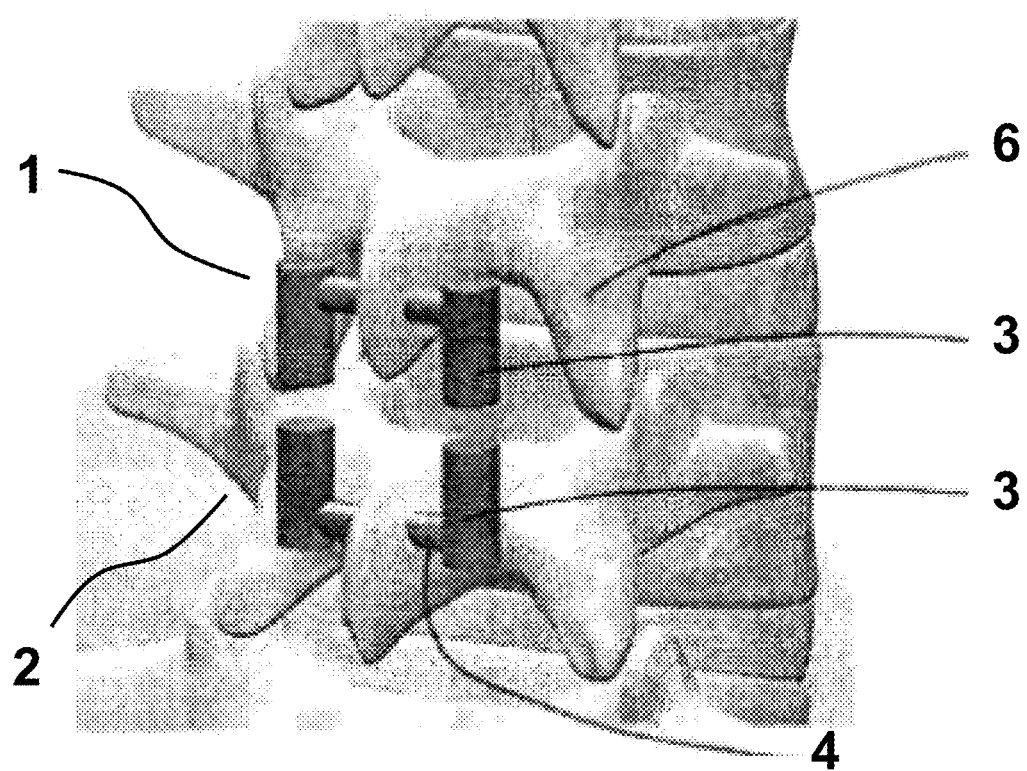
FIG. 10 is a posterior/side view of a device affixed to vertebrae, in which the device comprises vertebral attachments having a rod-shaped connecting component and pairs of magnets according to embodiments of the invention.
Figure 11:
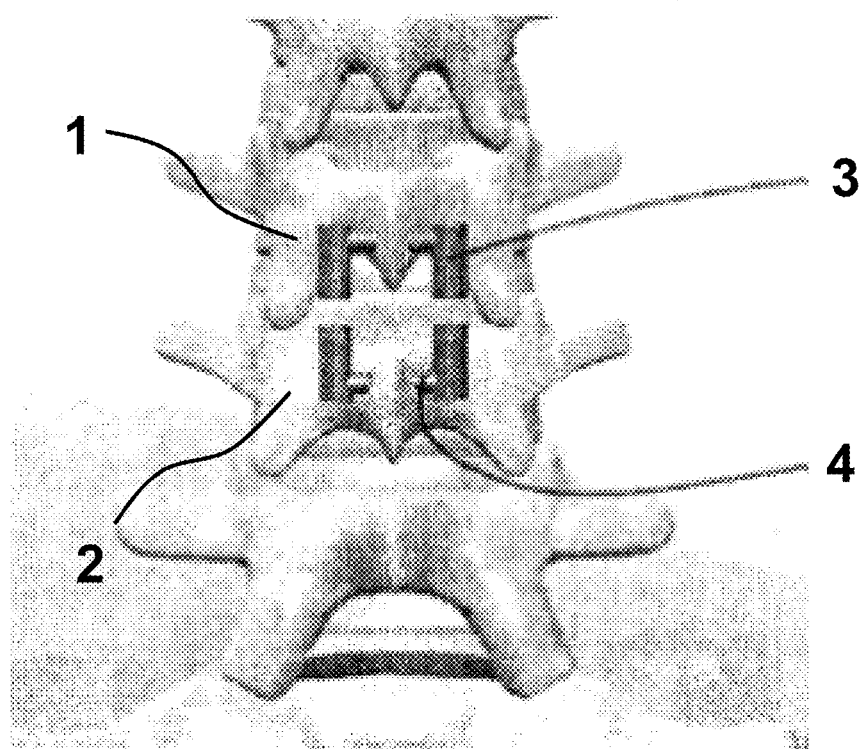
FIG. 11 is a posterior view of a device affixed to vertebrae, in which the device comprises vertebral attachments having a rod-shaped connecting component and pairs of magnets according to embodiments of the invention.

FIG. 6 shows vertebral attachments 1 and 2 in which the connecting components comprise a U-shaped extension 4. These vertebral attachments comprise a single magnet 3 in the shape of a quadrilateral. FIGS. 7 and 8 show the fixation of the vertebral attachments of FIG. 6 to the vertebrae 6. Further, FIG. 9 shows vertebral attachments 1 and 2 in which the connecting component comprises a rod-shaped extension 4, and is attached to pair of magnets 3 that are cylindrical in shape. FIGS. 10 and 11 show the fixation of the vertebral attachments of FIG. 9 to the vertebrae 6.

Figure 12:
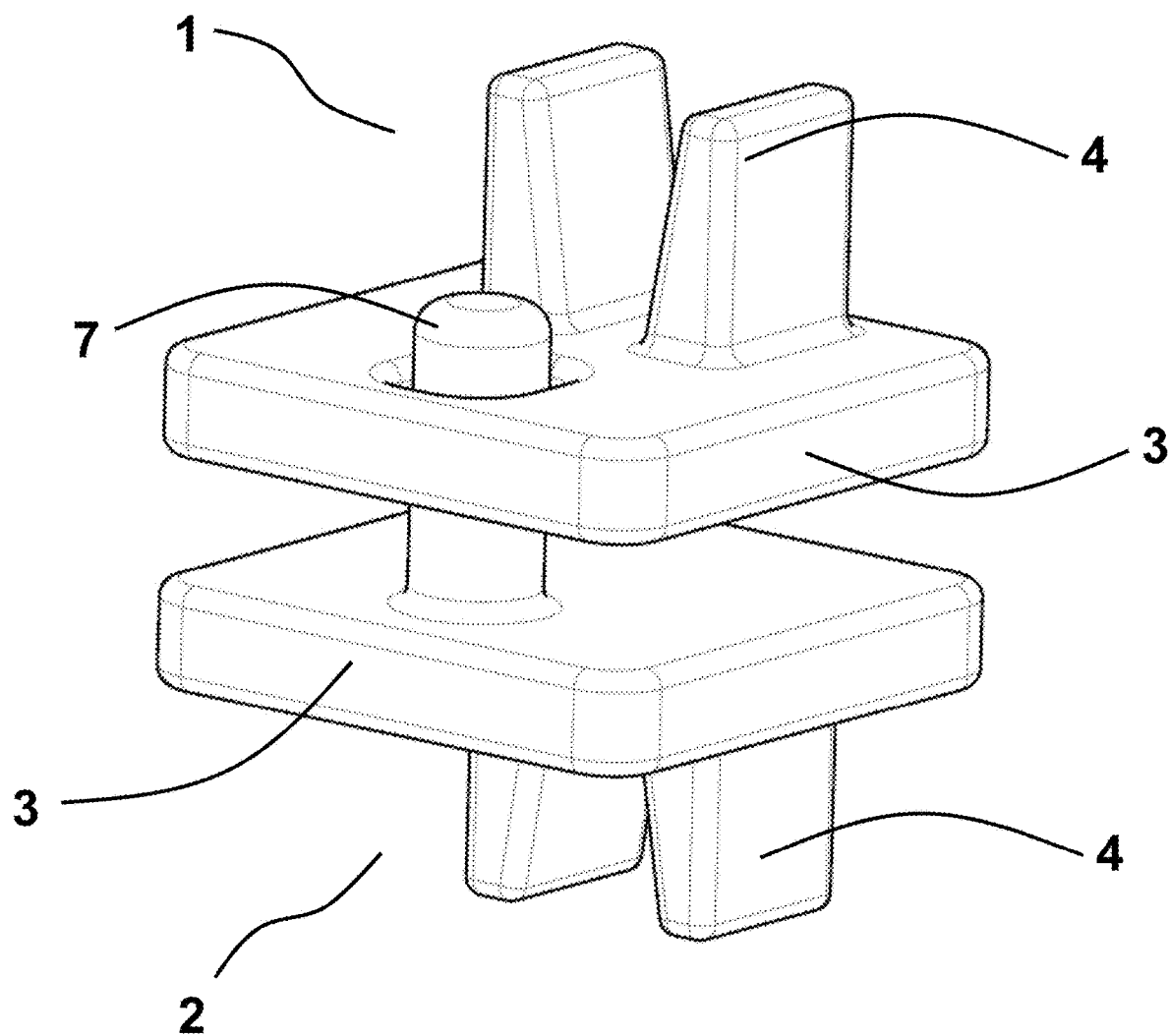
FIG. 12 is a device comprising vertebral attachments having a U-shaped connecting component and a single magnet with an alignment feature according to embodiments of the invention.
Figure 13:
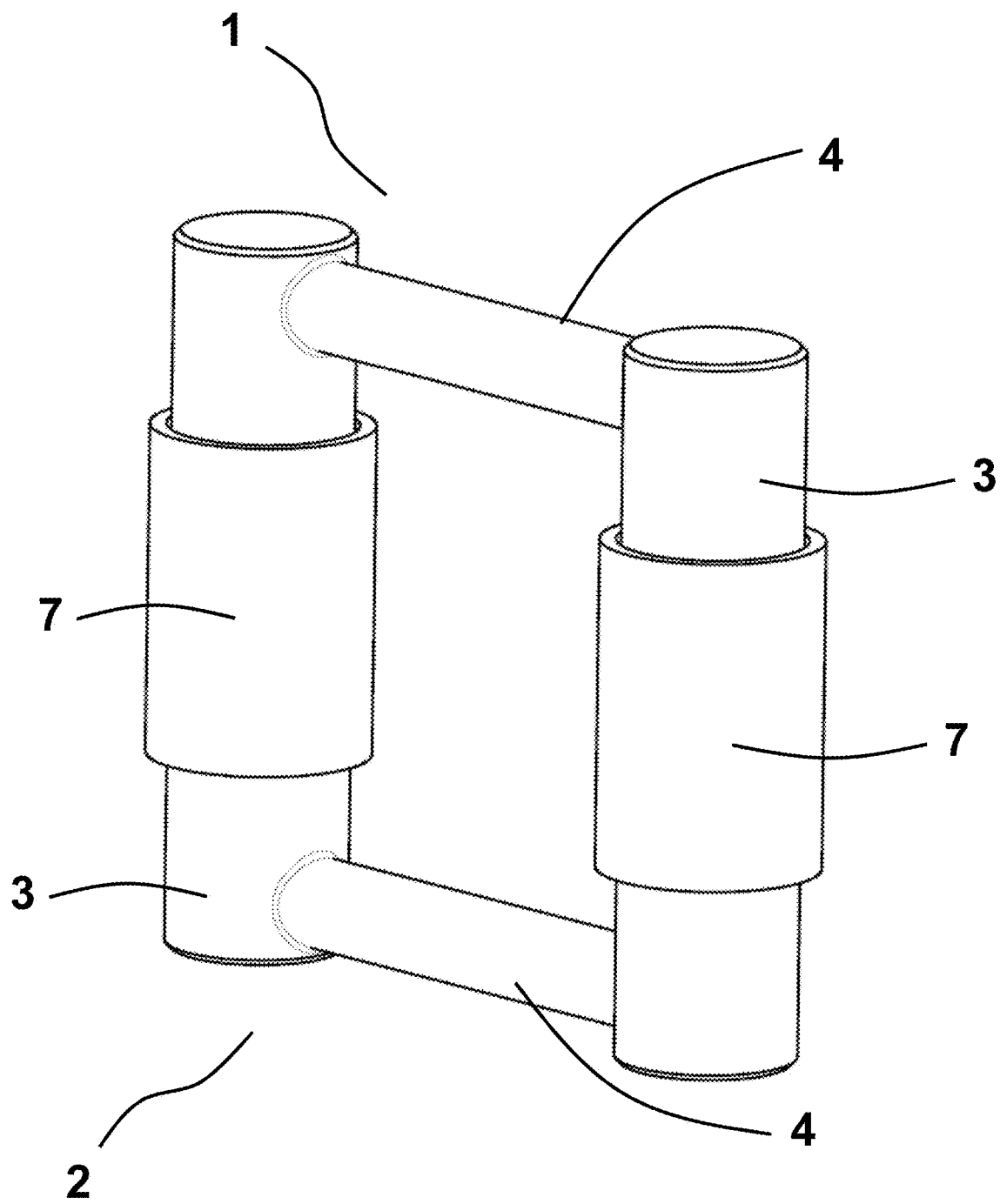
FIG. 13 is a device comprising vertebral attachments having a rod-shaped connecting component and pairs of magnets with an alignment feature according to embodiments of the invention.
Figure 14:
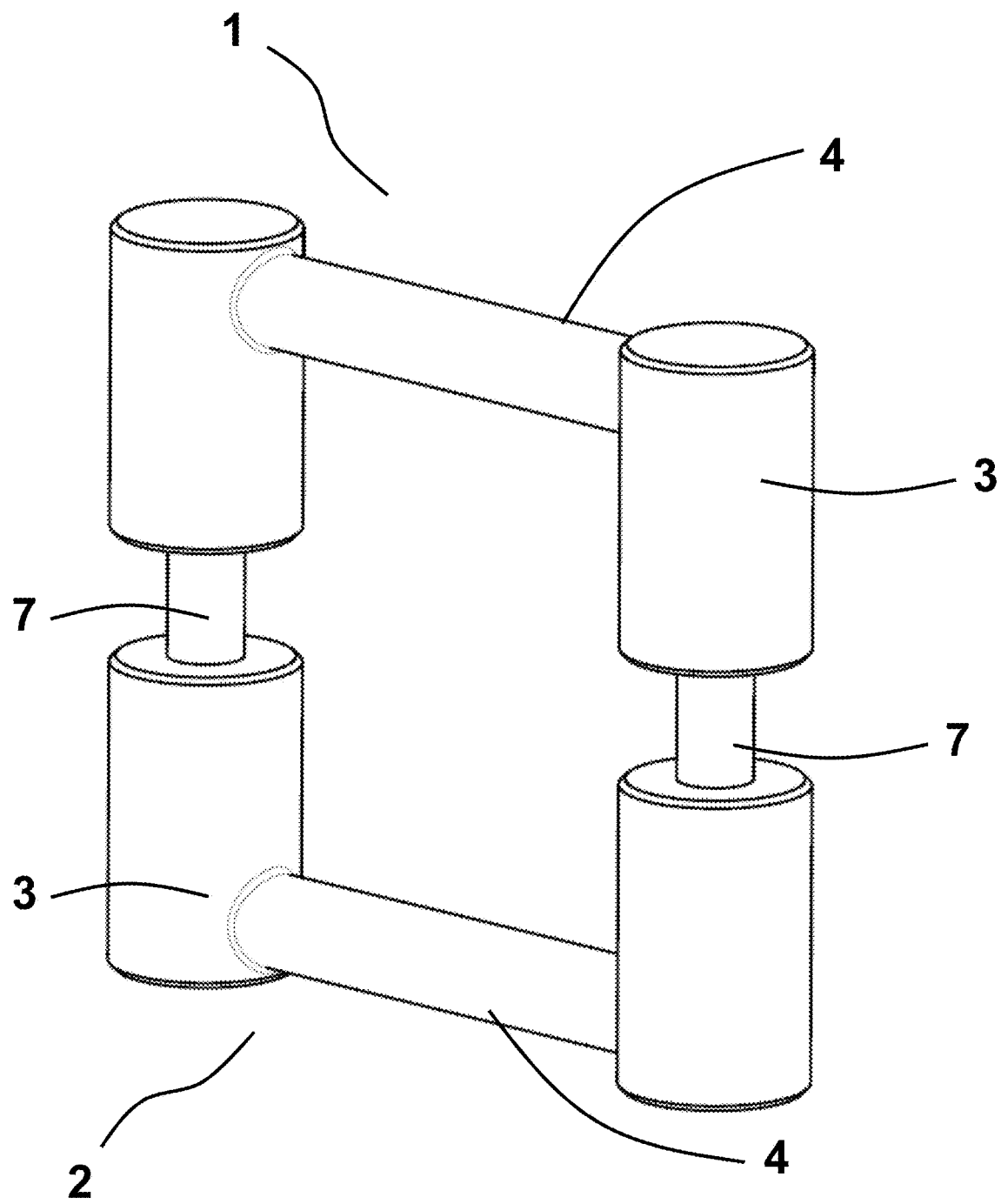
FIG. 14 is a device comprising vertebral attachments having a rod-shaped connecting component and pairs of magnets with an alignment feature according to embodiments of the invention.

In certain embodiments, the device may also have an alignment feature or features such as through pins, sleeves, sleeves with pins or blocking features such as hard stops or keels within slots to maintain axial (about the long axis of the spine) as well as rotary positioning of the device in one or more planes. Such embodiments are exemplified in FIGS. 12-14, in which each figure shows two vertebral attachments 1 and 2 that contain alignment feature 7.

In some embodiments, the device may have mechanisms such as cams or spacers to allow positioning of the magnets in order to achieve the desired maximum and minimum distractive (repulsion) or attractive (compression) forces obtained by the device during loading and motion.

Figure 15:
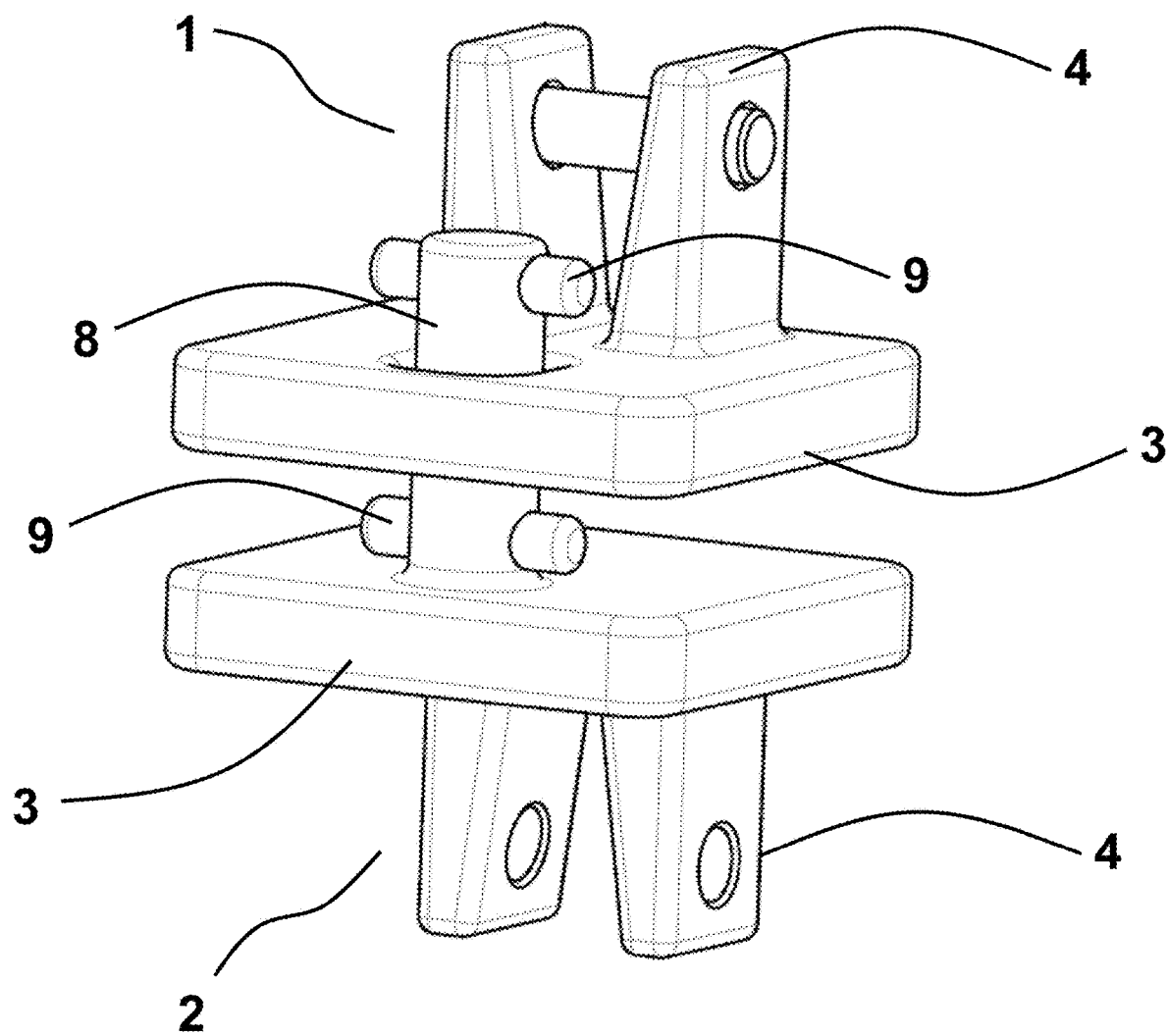
FIG. 15 is a device comprising vertebral attachments having a U-shaped connecting component and a single magnet with stops according to embodiments of the invention.
Figure 16:
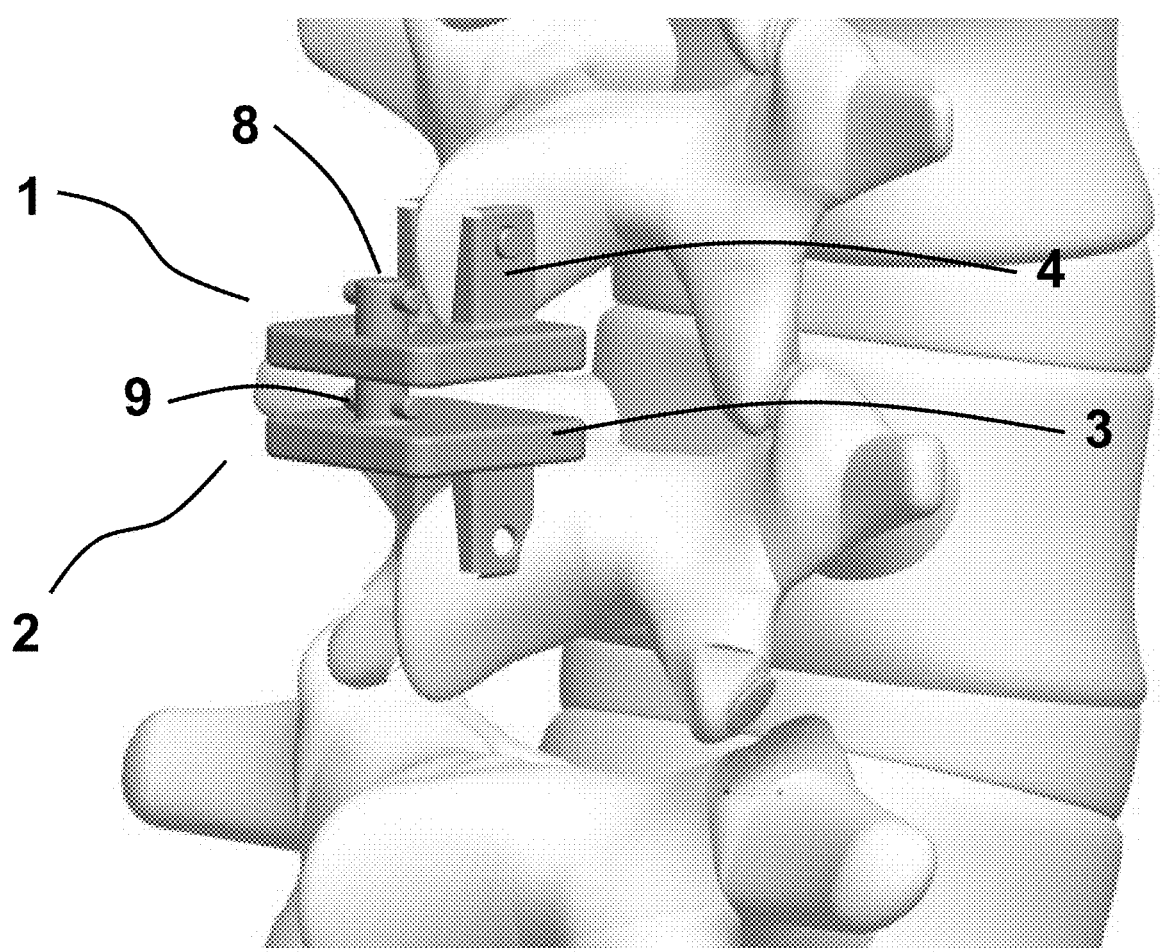
FIG. 16 is posterior view of a device affixed to vertebrae, in which the device comprises vertebral attachments having a U-shaped connecting component and a single magnet with stops according to embodiments of the invention.

In certain embodiments, the device may comprise a feature or features such as a hard stop or stops to limit the amount of spine flexion or extension allowed by the device, thereby limiting the maximum and minimum distractive (repulsive) and attractive (compressive) forces exerted by the device. An example is illustrated in FIGS. 15 and 16, which show two vertebral attachments 1 and 2 that contain holes (not shown) to accommodate a cylindrical rod 8 comprising stops 9.

Method of Treating Spinal Stenosis

The present invention also relates to methods of treating spinal stenosis, and/or methods of controlling or affecting or adjusting the interaction between adjacent vertebrae in the spine. In some embodiments, these methods involve maintaining a range of separation between aspects of adjacent vertebrae, whether through magnets that repulse, attract, or both.

The methods may comprise implanting the device of the present invention. The implantation may comprise surgically attaching each vertebral attachment to the appropriate vertebra. In some embodiments, the one or more magnets may be affixed to the vertebra directly, or may be attached to the vertebra via a connecting component as described above, or a combination thereof. Therefore, the implantation may comprise, for example, pinning, screwing, nailing or installing one or more rods to affix the one or more magnets to the vertebra.

One of ordinary skill in the art can determine where to position the vertebral attachments on each vertebra and on which vertebra to attach the vertebral attachment, based on the type of treatment that has been determined for the patient. In some embodiments, the vertebral attachment is affixed to the spinous process of the vertebra.

Detailed embodiments of the present devices, systems, and methods are disclosed herein; however, it is to be understood that the disclosed embodiments are merely illustrative of the devices, systems, and methods that may be embodied in various forms. In addition, each of the examples given in connection with the various embodiments of the systems and methods are intended to be illustrative, and not restrictive. Further, the drawing figures and photographs above are not necessarily to scale, some features may be exaggerated to show details of particular components. In addition, any measurements, specifications and the like shown herein are intended to be illustrative, and not restrictive. Therefore, specific structural and functional details disclosed herein are not to be interpreted as limiting to the appended patent claims, but merely as a representative basis for teaching one skilled in the art to variously employ the present devices, systems, and methods discloses herein. One skilled in the art will appreciate that numerous changes and modifications can be made to the invention, and that such changes and modifications can be made without departing from the spirit and scope of the invention.

What is claimed is:

1. A device for treatment of the spine, the device comprising a first vertebral attachment to a first vertebra and a second vertebral attachment to a second vertebra, wherein each vertebral attachment comprise:
(i) a set of one or more magnets; and
(ii) one or more connecting components that can affix the set of one or more magnets to a spinous process of the vertebra, wherein the one or more connecting components comprise:
(a) (i) an extension that comprises a ring-shape, wherein the extension comprising a ring-shape is designed to encircle a spinous process and wherein the extension comprising a ring-shape comprises a first hole and a second hole; and (ii) a rod or pin that is designed to pass through the first hole of the extension comprising a ring-shape, through the spinous process, and through the second hole of the extension comprising a ring-shape;
(b) (i) an extension that comprises an oval-shape, wherein the extension comprising an oval-shape is designed to encircle a spinous process and wherein the extension comprising an oval-shape comprises a first hole and a second hole; and (ii) a rod or pin that is designed to pass through the first hole of the extension comprising an oval-shape, through the spinous process, and through the second hole of the extension comprising an oval-shape;
(c) (i) an extension that comprises a U-shape, wherein the extension comprising a U-shape is designed to surround a spinous process on at least two sides and wherein the extension comprising a U-shape comprises a first hole and a second hole; and (ii) a rod or pin that is designed to pass through the first hole of the extension comprising a U-shape, through the spinous process, and through the second hole of the extension comprising a U-shape; or
(d) an extension that comprises a rod-shape, wherein the extension comprising a rod-shape is designed to fully extend through the spinous process;
wherein the set of one or more magnets of the first vertebral attachment is distinct from the set of one or more magnets of the second vertebral attachment;

wherein the set of one or more magnets of the first vertebral attachment attracts or repels the set of one or more magnets of the second vertebral attachment; and wherein the device further comprises an alignment feature to aid in positioning the first vertebral attachment relative to the second vertebral attachment, the alignment feature comprising a rod or pin, the alignment feature connecting to both the first vertebral attachment and the second vertebral attachment via a through-hole in one or both of the first vertebral attachment and the second vertebral attachment, and the alignment feature not comprising the set of one or more magnets.

2. The device of claim 1, wherein the set of one or more magnets comprise magnetic material comprising rare earth metals.

3. The device of claim 1, wherein the set of one or more magnets comprise a coating.

4. The device of claim 1, wherein the one or more connecting components comprises the extension that comprises a rod-shape.

5. The device of claim 1, wherein the one or more connecting components comprises the extension that comprises a ring-shape, an oval-shape, or a U-shape.

6. The device of claim 5, wherein the extension that comprises a U-shape is designed to surround the spinous process on at least three sides.

7. The device of claim 1, wherein the alignment feature further comprises a blocking feature comprising one or more hard stops, keels, or a combination thereof.

8. The device of claim 1, wherein the first vertebra and the second vertebra are adjacent.

* * * * *